United States Patent [19]
Laney et al.

[11] Patent Number: 5,540,232
[45] Date of Patent: Jul. 30, 1996

[54] METHOD AND APPARATUS FOR DISPLAYING PACER SIGNALS ON AN ELECTROCARDIOGRAPH

[75] Inventors: Bryan Laney, Lakewood; John A. Bachman, Dana Point, both of Calif.

[73] Assignee: Del Mar Avionics, Irvine, Calif.

[21] Appl. No.: 229,995

[22] Filed: Apr. 19, 1994

Related U.S. Application Data

[63] Continuation of Ser. No. 977,277, Nov. 16, 1992, abandoned.

[51] Int. Cl.$^6$ .................................................. A61B 5/0402
[52] U.S. Cl. .......................................... 128/697; 128/710
[58] Field of Search ................................. 128/696, 697, 128/710

[56] References Cited

U.S. PATENT DOCUMENTS

| | | | |
|---|---|---|---|
| 4,601,291 | 7/1986 | Boute et al. | 128/697 |
| 4,791,936 | 12/1988 | Snell et al. | 128/697 |
| 4,825,869 | 5/1989 | Sasmor et al. | 128/419 PT |
| 5,046,504 | 9/1991 | Albert et al. | 128/696 |
| 5,224,486 | 7/1993 | Lerman et al. | 128/696 |
| 5,305,761 | 4/1994 | Byrne et al. | 128/697 |

*Primary Examiner*—William E. Kamm
*Assistant Examiner*—Scott M. Getzow
*Attorney, Agent, or Firm*—J. D. Leimbach, Esq.; W. D. English, Esq.

[57] ABSTRACT

A system for monitoring the operation of a cardiac pacemaker and the response of the patient to the pacemaker includes an ARRHYTHMIAGRAPH that displays the occurrence of pacemaker signals in relation to overall QRS cycles and analyses the relationship of pacemaker signals to QRS cycles. A predetermined set of values are used to compare against measured QRS and pacemaker values. The result of the comparison is a determination of whether a QRS was initiated by a pacemaker signal. This determination is conveyed to display means where an ARRHYTHMIAGRAPH is used to illustrate the result in a visually discernible manner.

16 Claims, 4 Drawing Sheets

METHOD AND APPARATUS FOR DISPLAYING PACER SIGNALS ON AN ELECTROCARDIOGRAPH

This is a continuation of application Ser. No. 07/977,277 filed on Nov. 16, 1992, now abandoned.

BACKGROUND OF THE INVENTION

1. Field of the Invention

This invention relates to the field of Holter Monitoring and, more specifically, to the analysis and display of the QRS intervals and associated pacer signals on an electrocardiograph.

2. Description of the Prior Art

The prior art has dealt with the need for the detection of pacemaker signals within an electrocardiogram and with the display of a large number of QRS signals by means on an electrocardiograph. Such a system was taught by U.S. Pat. No. 4,336,810 issued to Anderson et al. and included features such as scanning Holter tapes at high speed to produce Holter displays and an associated proprietary electrocardiograph termed the ARRHYTHMIAGRAPH. The ARRHYTHMIAGRAPH™, which is a trademark of the assignee of Anderson et al., presently is known to appear graphically on the side or bottom of an ECG display to depict ectopic patterns as well as changes in rate and rhythm by usage of a series of bar graphs where each bar represents the length of time from one QRS to the next QRS. The ARRHYTHMIAGRAPH has proven useful in providing a means of surveying a large number of categorized heartbeats simultaneously. However, the ARRHYTHMIAGRAPH has until the present time has only been used with naturally occurring ECG signals and has not been shown to be useful with respect to pacemaker signals.

U.S. Pat. Nos. 4,291,703 and 4,532,934 issued to Kelen, each presented a system that permitted recording and analysis of heartbeats as well as pacemaker generated pulses. While successful in detecting pacemaker signals this system did not satisfy the need for graphically viewing large numbers of pacemaker signals in relation to QRS intervals.

Various types of pacemakers are available today. Among these are pacemakers which provide for either atrial stimulus, ventricular stimulus or both. Pacemakers are also currently available with defibulators. Electrocardiographic systems that analyze human subjects who have pacemakers must, therefore, have the capability of identifying various types of electronic signals that can originate within a pacemaker. Unfortunately, conventional systems currently available can not provide analysis results of affects pacemakers signals have on QRS intervals in a manner that is visually discernible over a large number of beats.

As can be seen by the foregoing discussion, there remains a need within the prior art for a system that can provide analysis results of pacemakers signals effect on QRS intervals that are visually discernible simultaneously over a large number of beats. The present invention not only identifies various pacemaker signals, it presents an ARRHYTHMIAGRAPH displaying 360 QRS cycles and analyzes the affect of pacemaker signals on the QRS cycle. The present invention addresses the shortcoming of the aforementioned prior art in that it provides a manner by which large numbers of pacemakers signals can be viewed to identify their relationship to the relative QRS cycles.

SUMMARY OF THE INVENTION

The present invention fills the need for a system that can provide an ARRHYTHMIAGRAPH with the capability of displaying results that have been modified in relation to pacemaker signals. In the preferred embodiment a digital computer workstation will read data from a two channel cassette tape. The first channel contains ECG data while the second includes a modified pacemaker signal to permit analysis. Data from the tape is digitized prior being input to a digital computer. The analysis performed includes comparison of a predetermined set of numbers indicative of normal ranges with those actually measured. The occurrence of QRS intervals and the initiation of pacemaker signals are compared in relation to the respective counterparts that are actually measured during the course of analysis. The analysis results are combined and output to the display in the form of an ARRHYTHMIAGRAPH that contains measurements and their relationship to the predetermined norm in the form of visually discernible bars graphs that are color coded.

It is an object of the present invention to disclose a system having an arrhythmia analyzer that illustrates the relation between pacemaker signals and QRS cycles.

It is an object of the present invention to teach a an accelerated method of measuring and assessing heartbeat morphologies.

DESCRIPTION OF THE PREFERRED EMBODIMENT

Figure 1:
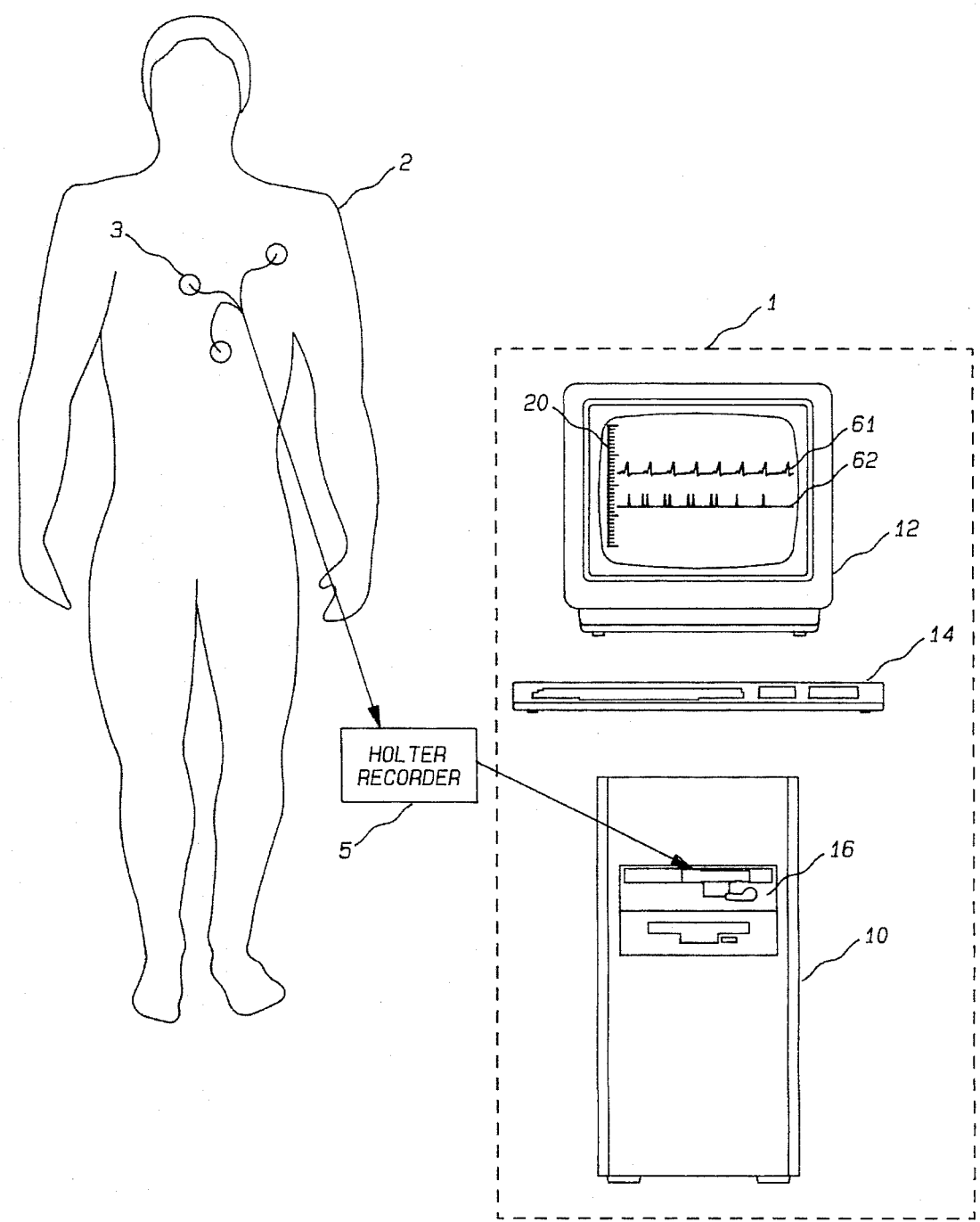
FIG. 1 is an illustration of the general operation of the present invention.

Turning now to the drawings and specifically to FIG. 1, which is an illustration of the general operation of the present invention, subject 2 wears electrodes 3 which detect bioelectric signals of the human heart and transmit these signals to Holter recorder 5. Workstation system 1 which embodies the present invention, digital computer 10 with high resolution display 12 and keyboard 14. Holter recorder 5 records electrocardiographic signals subject patient 2 via electrodes 3, which recording is played back to the digital computer 10 in the workstation 1. The recorded data is digitized prior analysis by computer 10. The holter recorder 5 used in the present invention actually creates a pacecorder tape 6 record, which in the present invention contains a first channel with ECG data and a second channel which contains recorded pacemaker activity. The pacecorder tape 6 is placed within the playback means 16 within workstation 1. The pacemaker activity contained on the second channel is modified prior being analyzed and displayed. These modified pacemaker pulses, which are referred to hereinafter as pseudo pacemaker pulses 25, are modified from the actual pacemaker signal for more accurate detection and scanning. The first and second channels are digitized prior to analysis by the digital computer 10. The analysis consists of arrhythmia analysis and pacecorder analysis the results of which are used to generate display 12.

Figure 2A:
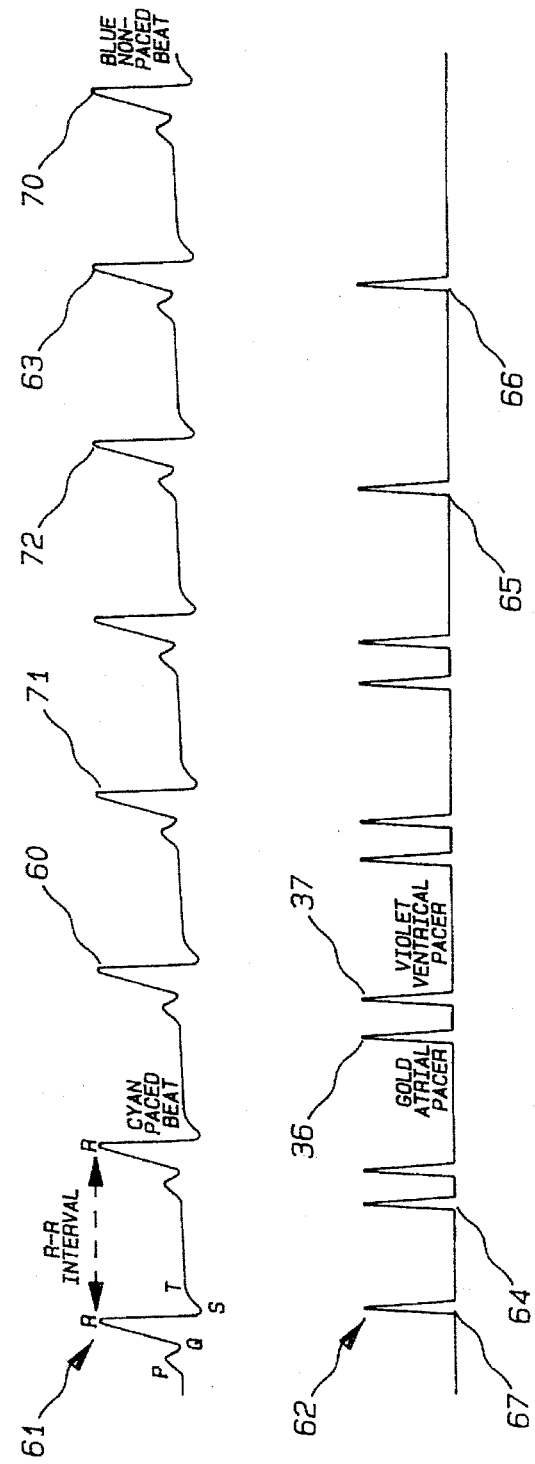
FIG. 2a an illustration of two displayed channels for QRS cycles and pacer signals.

Referring to FIG. 2a which is a diagram of two display channels. The first channel 61, is a trace of detected QRS intervals, while the second channel 61 is a trace of detected pacemaker signals. The pacemaker signals are either atrial pacemaker signals 36 or ventricular pacemaker signals 37. Beats are labeled as either dualed paced 64, atrial paced 65, ventricular paced 66, pacer signals not within the foregoing definitions 67 and normal beats 70. Looking at the display of FIG. 2a it is possible to see QRS intervals 60 along with associated pacemaker signals on the second channel 62 with a great deal of detail. Although relatively few beats can be observed at any given moment. A novel feature of the present invention is to color code the results of analysis on the display screen. Thus on FIG. 2a, the second channel displaying detected pacemaker signals is color coded to reflect the relevance of that pacemaker signal to its respective QRS interval. Beats classified as normal 31 are distinguished from other beats by color coding them blue. After the occurrence of a pacemaker signal, beats are then classified as paced beats 32 and color coded as cyan. In the event that a beat is paced by both an atrial pacer signal 36 and ventricular pacer signal 37, the beat is classified as dual paced 34 and the area between the atrial pacer signal 36 and the ventricular pacer signal 37 is color coded gold. After a ventricular pacer signal 37 the beat is classified as post ventricular 33 and color coded as violet. In the event that an atrial pacer signal 36 is detected but no ventricular pacer signal 37 is detected, then the color code is white. By having the detected pacer signals code to make them visually discernible, results of analysis are immediately available to the user.

Figure 2B:
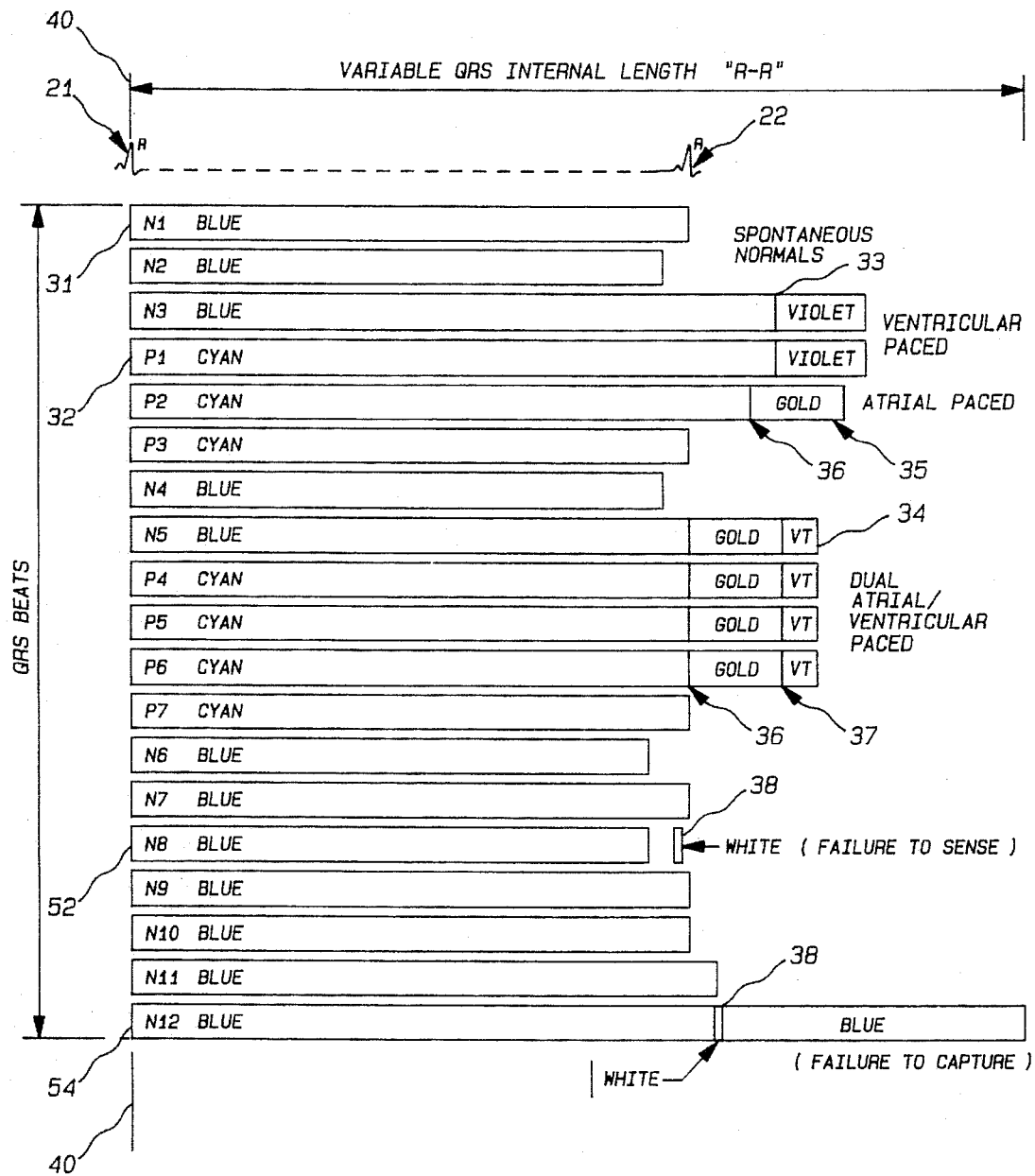
FIG. 2b is an enlarged view of the ARRHYTHMIAGRAPH taught by the present invention with pacemaker signals shown in relation to QRS intervals.

Referring now to FIG. 2b is an enlarged view of the ARRHYTHMIAGRAPH 20 taught by the present invention, pacemaker signals 25 are shown in relation to QRS intervals. The individual bar graphs of ARRHYTHMIAGRAPH 20 indicate the length of time between detected QRS's. The individual bar graphs that comprise ARRHYTHMIAGRAPH 20 have been sectioned to illustrate the time of occurrence of atrial pacemaker signals 36 and ventricular pacemaker signals 37 in relation to QRS intervals. While this sectioning is considered a novel element of the present invention, the preferred embodiment of the present invention uses color coding to make the sectioning of ARRHYTHMIAGRAPH 20 more visually discernible to the operator.

Beats classified as normal 31 are distinguished from other beats by color coding them blue. After the occurrence of a pacemaker signal, beats are then classified as paced beats 32 and color coded as cyan. In the event that a beat is paced by both an atrial pacer signal 36 and ventricular pacer signal 37, the beat is classified as dual paced 34 and the area between the atrial pacer signal 36 and the ventricular pacer signal 37 is color coded gold. The bar graph after a ventricular spike is classified as post ventricular 33 and bar coded as violet. In the event that an atrial pacer signal 36 is detected but no ventricular pacer signal 37 is detected, then the bar graph after the atrial pacer signal 36 is classified as post atrial 35 and that portion of the bar graph after the atrial pacer signal 36 is color coded white 35. In the event that a pacer signal is detected after a QRS has begun a dot follows that bar graph on the ARRHYTHMIAGRAPH. In the preferred embodiment, various colors are used on display 12 to illustrate the analysis results relating to QRS intervals and pacemaker signals.

Still referring to FIG. 2b, the ARRHYTHMIAGRAPH of the present invention display much more information regarding the analyzed beats and the position of the pseudo pacer pulses in the interval between detected beats than previous ARRHYTHMIAGRAPH. This new information is shown not only with the use colors, but with the sequence in which these colors are presented. On the ARRHYTHMIAGRAPH each line begins with a detected QRS and ends with the next detected QRS. The beginning of an interval between beats is generally defined by the onset line 40 in FIG. 2b. Each bar graph represents the time interval between consecutive detected QRS cycles. Therefore, each detected QRS is at the end of one bar graph and the beginning of the next. The initial color of a line is determined by the label that was placed on the previous beat that terminated the last line. If no pseudo pacer pulses 25 are detected on channel two, each line contains only one color and the Arrhythmiagraph would look Referring still to FIG. 2b, the original colors of blue for normal sinus beats 31, red for ventricular ectopics 28, green for superventricular ectopics 29, yellow for unknown 30, white for calibration pulses 27 and gray for artifact 26 have been increased by the addition of three new colors. The initial color of an ARRHYTHMIAGRAPH 20 line is cyan if the previous beat was initiated in any way by a pacemaker and is therefore labeled a paced beat 32. If a pseudo pacer pulse is detected to be within a predetermined range to the next QRS beat, then that beat will be classified as a ventricular paced beat 33 and the remainder of that line of the ARRHYTHMIAGRAPH will be color coded at a point on the line proportional to the position of detection of the ventricular pseudo pacer pulse 37. If several beats in a row are labeled ventricular paced beats, the effect of this coloring scheme is to produce violet bars at the right end of cyan lines whose width represents the delay between the ventricular pseudo pacer pulse 37 and the paced beats they initiated. If both an atrial pacemaker signal 36 and a ventricular pacemaker signal 37 are detected within a QRS within a predetermined timing relationship, the beat will be labeled as a double paced beat, generally referred to as a dual paced beat 34. The color of the ARRHYTHMIAGRAPH upon detection of a dual paced beat 34, will turn from its original color from the onset line 40 to gold at a point proportional to the position of the Atrial pacemaker signal 36 in the R to R interval. The line will then turn from gold to violet at the occurrences of ventricular pacemaker signal. The result of this coloring scheme is to show a gold bar on the ARRHYTHMIAGRAPH line with a width that is proportional to the delay between the atrial pacemaker signal 36 and the ventricular pacemaker signal.

Figure 3A:
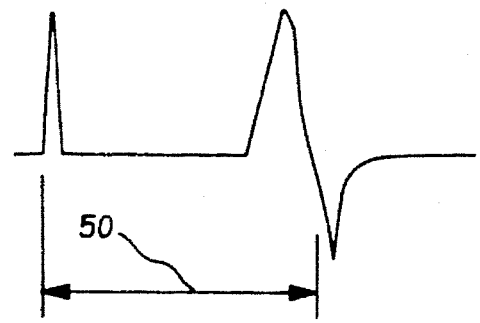
FIG. 3a is a diagram of the window used for determination of a paced beat.

Referring now to FIG. 3a in conjunction with FIG. 2b, the QRS intervals labeled paced 32 and indicated in cyan have achieved this status as a result of comparison steps with predetermined coefficients. In order for a beat to be labeled paced 32 the R wave of a QRS cycle must have been detected within the paced window 50. In the preferred embodiment wherein pacecorder tape 6 is an analog recording for ventricular pacemaker signals 37, the paced window 50 would be between $-40<T<120$ milliseconds, here T is the time in which the R wave is detected after a ventricular pacemaker signal 37 is detected. For atrial pacemaker signals 36 the paced window is $100<T<444$ milliseconds for analog pacecorder tapes 6. In an embodiment employing DAT tapes and recorders the paced window 50 would be in the vicinity of $0<T<120$ milliseconds. Here, analog tape embodiment have tape head skew that must be accounted for, therefore the seemingly impossible $-40$ in the paced window is quite realistic. DAT tape while providing more accurate recordings is presently not cost effective. Thus analog tape is the preferred embodiment. However the present invention is equally used with any storage medium, whether it be analog tape, DAT tape, magnetic disc, optical disc, magneto optical disc or memory card technology. The paced window 50 for atrial pacemakers devices remains pretty much the same for DAT tape embodiments due to physiological inconsistencies of the subject 2.

Figure 3B:
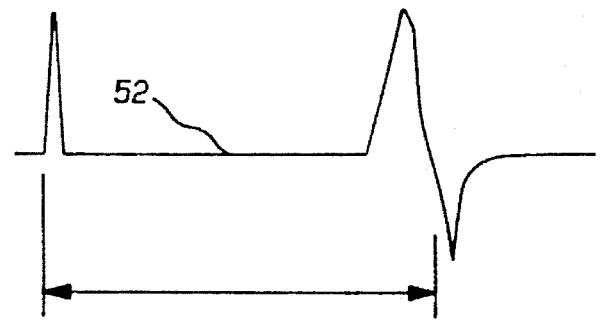
FIG. 3b is a diagram of the window used for determination of a failure to capture labeled beat.
Figure 3C:
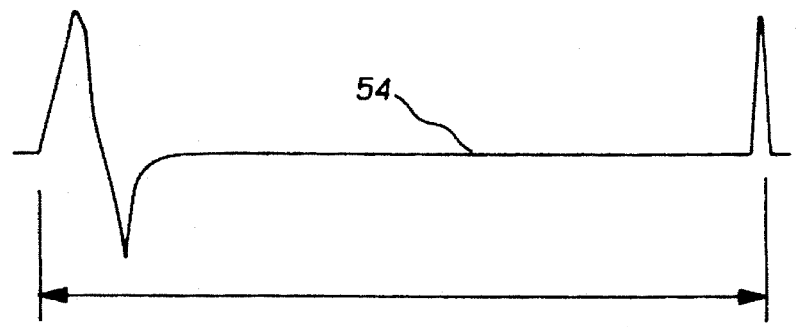
FIG. 3c is a diagram of the window used for determination of a failure to sense labeled beat.

Referring now to FIG. 3b and 3c, included as additional features of the present invention are the determination of failure to capture beats 42 and failure to sense 44 beats. These occur when the relative position of pseudo pacemaker pulses in the R to R interval are not within predetermined limits, and therefore, are not associated with a QRS, i.e. QRS closest to the pseudo pulse is not a paced beat 32. The case of a failure to sense 44 is shown in FIG. 3c where the pacemaker signal is measured within the predetermined fail to sense window 54, this is predetermined in the preferred embodiment as greater than 140 milliseconds after the associated QRS. If the pseudo pacemaker pulse occurs after the QRS within the fail to senses window 54, the pseudo pacemaker pulse will show as a white pacer dot 39 to the right of the bar in ARRHYTHMIAGRAPH 20 as can be seen in FIG. 2b.

Referring now to FIG. 3b, which illustrates the case of a failure to capture 42, the a pseudo pacemaker pulse 25 occurs before the QRS by an amount too large for the pseudo pacemaker signal 25 to be considered an atrial pacemaker signal 36. Therefore the pseudo pacemaker signal 25 is classified as a failure to capture 42, which is displayed on the ARRHYTHMIAGRAPH as a white dot on the line within the ARRHYTHMIAGRAPH that represents the interval which the pseudo pulses is between. In order to be labeled as a failure to capture 42 the R wave of a detected QRS must not fall within the failure to capture window 52. Relative to ventricular pacemaker signals 37 this window is −40<T143 for analog tape devices and 0<T<130 for DAT tape devices. For atrial pacemaker signal 36, the failure to capture window 42 is 100<T<588 milliseconds.

Referring to FIG. 3c a failure to sense 44 is detected if the pacer signal is within the ranged defined by the failure to sense window 54 of the measured QRS. Here, the failure to sense window is 132<T<($P_{intvl}$−148 milliseconds), where $P_{intvl}$ is the minimum pacer interval as defined by the manufacturer of the pacemaker. It should be noted that $P_{intvl}$ can vary for atrial pacemaker signals 36 and ventricular pacemaker signals 37.

Figure 3D:
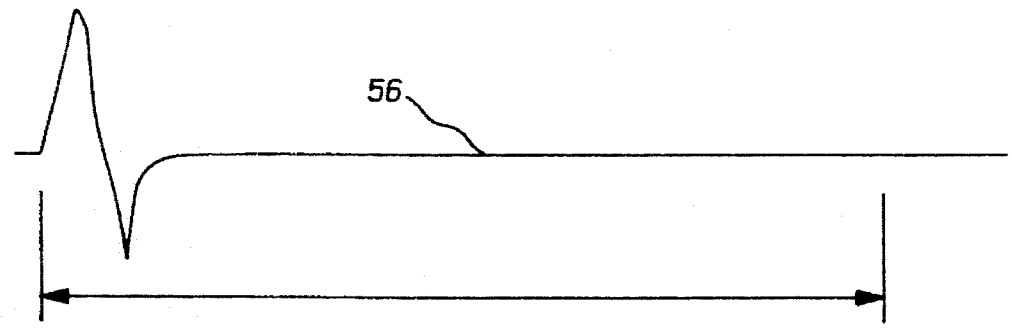
FIG. 3d is a diagram of the window used for determination of a failure to output labeled beat.

Referring now to FIG. 3d a failure to output 46 occurs when neither a QRS or a pseudo pacemaker pulse 25 is not detected at all within the predetermined time frame defined as the failure to output window 56. This situation is classified as a failure to output 46. The failure to output window is defined in terms of the minimum paced rate interval (MPRI) for ventricle pacemaker signals 0<T<(MPRI+263 milliseconds). For atrial pacemaker signals, the failure to output window is defined as either 0<T<MPRI or 0<T<(MPRI+444 milliseconds)

It should be noted that while the present invention as disclosed herein defines specifically the embodiment most preferred by the inventors numerous alterations are attainable. These could include varying storage technologies as well different types of pacemakers. Within the various types of embodiments there still exists the generic principles of the present invention.

The foregoing detailed description is intended to be illustrative of the preferred embodiment as envisioned by the inventors. Additional embodiments will be obvious to those skilled in the relevant arts without departing form the scope of the invention. Therefore, the present invention is not limited to the preferred embodiment as detailed herein, but by the claims appended, hereto.

What is claimed is:

1. A system for monitoring and reporting signals indicative of a patient's pacemaker operation and of said patient's ECG response to pulses from said pacemaker as revealed by a time ordered relationship between said pacemaker pulses and QRS cycles and intervals of said patient's ECG, comprising:

electrode sensing means for detecting said patient's ECG and said pacemaker pulses;

recorder means, coupled to said sensing means, for storing said patient's ECG on a first channel and for storing said pacemaker pulses indicative of said patient's pacemaker operation on a second channel;

computer means, coupled to said recorder means, for analyzing data recorded by said recorder means;

playback means, electrically interfaced with said computer means, for converting said first and said second channel data into a format usable by said computer means;

analysis means, within said computer means, for analyzing data from said first channel and said second channel and establishing a time ordered relationship between data from said first channel and data from said second channel;

comparison means, within said computer means, for comparing said time ordered relationship from said first and said second channels with a set of predetermined, computer stored, time duration values indicative of normalcy of said QRS intervals of said ECG with respect to said pacemaker pulses;

display means, coupled to said computer means, for displaying results of said analysis means and said comparison means in a manner that illustrates said time ordered relationship between said patient's ECG on said first channel and said pacemaker pulses on said second channel in a visually discernible manner, whereby an ECG representation is produced that indicates color coded results of said analysis means by illustrating points within said QRS intervals wherein said pacemaker pulses are detected and further produces a visually discernible indication of an estimated effect of said pacemaker pulse upon initiation of a QRS cycle, and wherein said color coded results can further delineate and differentiate between a paced beat and an unpaced beat.

2. The system of claim 1, wherein said set of predetermined values includes indicators for the occurrence of an atrial pacemaker pulse relative to a normal QRS interval.

3. The system of claim 1, wherein said set of predetermined values includes indicators for the occurrence of a ventricular pacemaker pulse relative to a normal QRS interval.

4. The system of claim 1, wherein said set of predetermined values includes indicators for a failure-to-capture event if a QRS cycle is not detected within a predefined time span of a detected pacemaker pulse.

5. The system of claim 1, wherein said set of predetermined values includes indicators for a failure-to-sense event if a pacemaker pulse is not found within a predefined time span of a detected QRS cycle.

6. The system of claim 1, wherein said set of predetermined values includes indicators for a failure-to-output event to determine the absence of both a QRS cycle and a pacemaker pulse within a predefined time span.

7. A method for producing a graphical display that illustrates the relationship of a pacemaker pulse to a QRS cycle and a QRS interval in an ECG signal, comprising the steps of:

recording ECG signals and pacemaker pulses of a patient using electrode sensing means;

conveying said ECG signals of said patient in a digitized form to computer means capable of storing and analyzing digitized ECG signals;

creating a predetermined set of time duration values that are indicative of normal ranges of occurrences of said pacemaker pulses relative to said QRS cycles and intervals;

detecting both said QRS cycles and intervals and also said pacemaker pulses within said digitized ECG signals;

comparing measured occurrences of said pacemaker pulses relative to measured occurrences of said QRS cycles and intervals, and comparing each said measured occurrence with its respective counterpart within said predetermined set of time duration values;

determining points within said QRS intervals where said pacemaker pulses have been detected based on results of said comparing step; and displaying results of said determining step in a visually discernible manner by means of a graphical representation illustrating points within said QRS intervals of said ECG where pacemaker pulses have been detected.

8. The method of claim 7, wherein said set of predetermined values includes at least one reference value for an atrial pacemaker pulse.

9. The method of claim 7, wherein said set of predetermined values includes at least one reference value for a ventricular pacemaker pulse.

10. The method of claim 7, wherein said set of predetermined values includes at least one reference value for both atrial and ventricular pacemaker pulses.

11. The method of claim 7 wherein said recording step is accomplished by employing recording means that is any member selected from the group of: analog tape, digital tape, magnetic disc, magneto-optical disc and memory card technology.

12. A system for providing an indication of pacemaker operation relative to QRS cycles and intervals in an ECG, comprising:

recording means for recording analog ECG signals on a first channel and pacemaker pulses on a second channel of a patient using electrode sensing means;

digital means, coupled to said recording means, for converting said analog ECG signals into a digital form;

computer means, coupled to said digital means, for analyzing data recorded by said recording means;

analysis means, within said computer means, for providing a time ordered relationship between said first channel of ECG signals and said second channel of pacemaker pulses; and means, coupled to and responsive to said analysis means, for providing a visually discernable indication and display of said time ordered relationship between said recorded ECG signals in said first channel and said pacemaker pulses in said second channel, wherein each said channel further includes not only a single pace display means for producing graphical illustrations of QRS signals that have been resisted by a single pacemaker pulse, but also a double paced display means for producing said graphical illustrations of QRS signals that have been assisted by a pair of pacemaker pulses.

13. The system according to claim 12, wherein said means responsive to said analysis means provides visual indications of results obtained by said analysis means by means of color coded graphics.

14. The system according to claim 12, wherein said means responsive to said analysis means further comprises:

first means for displaying a graphical representation of a large number of QRS cycles; and second means for displaying a limited number of QRS cycles and associated pacemaker signals.

15. A system for monitoring and reporting signals indicative of a heart patient's pacemaker operation and of said patient's ECG response to pulses from said pacemaker as revealed by a time ordered relationship between said pacemaker pulses and QRS cycles and intervals of said patient's ECG, comprising:

electrode sensing means for detecting said patient's ECG and said pacemaker pulses;

data recording means, coupled to said sensing means, for storing said patient's ECG data on a first channel and for storing said pacemaker pulse data indicative of said patient's pacemaker operation on a second channel;

computer means, coupled to said recording means, for analyzing data recorded by said recording means;

playback means, electrically interfaced with said computer means, for converting said first and said second channel data into a format usable by said computer means;

analysis means, within said computer means, for analyzing data from said first channel and said second channel and establishing a time ordered relationship between data from said first channel and said second channel;

comparison means, within said computer means, for comparing said time ordered relationship from said first and said second channels with a set of predetermined, time duration values indicative of normalcy for said QRS intervals of said ECG and said pacemaker operation; and display means, coupled to said computer means, for displaying results of said analysis means and said comparison means in a manner that illustrates said time ordered relationship between said patient's ECG on said first channel and said pacemaker pulses on said second channel in a visually discernible manner, whereby an ECG representation is produced that indicates color coded results of said analysis means by illustrating points within said QRS intervals wherein said pacemaker pulses are detected and further produces a visually discernible indication of an estimated effect of a pacemaker pulse upon initiation of a QRS cycle, and wherein said color coded results includes separate codes for an atrial paced beat, a ventricular paced beat, a dual paced beat, an unpaced beat, and an undetected beat.

16. A system for providing an indication of pacemaker operation relative to QRS cycles and intervals in an ECG, comprising:

recording means for recording analog ECG signals and pacemaker pulses of a patient using electrode sensing means;

digital means, coupled to said recording means, for converting said analog ECG signals into a digital form;

computer means, coupled to said digital means, for analyzing data recorded by said recording means;

analysis means, within said computer means, for providing a time ordered relationship between a first channel of ECG signals and a second channel of pacemaker pulses; and means, coupled to and responsive to said analysis means, for providing a visually discernable indication and display of said time ordered relationship between said recorded ECG signals in said first channel and said pacemaker pulses in said second channel, wherein said display means further includes a normal sinus beat means for determining instances where a pacemaker pulse has not assisted in generating a QRS signal.

* * * * *